US008969290B2

(12) United States Patent
Rolle et al.

(10) Patent No.: US 8,969,290 B2
(45) Date of Patent: Mar. 3, 2015

(54) MATRIX SCAFFOLD WITH ANTIMICROBIAL ACTIVITY

(71) Applicants: Marsha Rolle, Worcester, MA (US); Fioleda Prifti, Worcester, MA (US); Chris Malcuit, Kent State, OH (US); Terri Anne Camesano, Worcester, MA (US); Tanja Dominko, Worcester, MA (US); Denis Kole, Worcester, MA (US)

(72) Inventors: Marsha Rolle, Worcester, MA (US); Fioleda Prifti, Worcester, MA (US); Chris Malcuit, Kent State, OH (US); Terri Anne Camesano, Worcester, MA (US); Tanja Dominko, Worcester, MA (US); Denis Kole, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 13/928,245

(22) Filed: Jun. 26, 2013

(65) Prior Publication Data

US 2013/0345118 A1 Dec. 26, 2013

Related U.S. Application Data

(60) Provisional application No. 61/664,386, filed on Jun. 26, 2012.

(51) Int. Cl.
*A61L 27/54* (2006.01)
*C07K 14/78* (2006.01)
*C07K 14/47* (2006.01)
*C12N 15/62* (2006.01)

(52) U.S. Cl.
CPC .................. *A61L 27/54* (2013.01); *C07K 14/78* (2013.01); *C07K 14/4723* (2013.01); *C12N 15/62* (2013.01); *C07K 2319/00* (2013.01)
USPC ........................................... 514/2.3; 530/350

(58) Field of Classification Search
CPC ............... A61K 27/54; A61K 2430/16; C07K 2319/00; C07K 2319/01; C07K 2319/33; C07K 14/4723; A61L 27/54
USPC ...................................... 514/3.2, 2.3; 530/350
See application file for complete search history.

(56) References Cited

U.S. PATENT DOCUMENTS

| 7,452,864 | B2 | 11/2008 | Stahle-Backdahl et al. |
| 7,659,366 | B2 | 2/2010 | Ellen et al. |
| 8,110,658 | B2 | 2/2012 | Harris et al. |
| 2009/0214649 | A1 | 8/2009 | Gazit et al. |

FOREIGN PATENT DOCUMENTS

| EP | 0704532 A2 | 4/1996 |
| WO | 2010091294 A2 | 8/2010 |
| WO | 2011036171 A1 | 3/2011 |

OTHER PUBLICATIONS

Ghannad (Design and Synthesis of Collagen-binding Anti-microbial Proteins-Thesis, created Apr. 25, 2011).*
Stie et al. (Journal of Leukocyte Biology, vol. 82, 2007: p. 161-172).*
Sun et al. (Growth Factors, Oct. 2007: 25(5):309-18).*
International Search Report and Written Opinion dated Feb. 3, 2014 for PCT/US2013/047975.

* cited by examiner

*Primary Examiner* — James H Alstrum Acevedo
*Assistant Examiner* — Tara Martinez
(74) *Attorney, Agent, or Firm* — Burns & Levinson, LLP; Janine M. Susan

(57) ABSTRACT

The invention provides a scaffold of extracellular matrix polymers with recombinant chimeric peptides tethered thereto. The invention also provides recombinant chimeric peptides of antimicrobial peptides and extracellular matrix binding domains. The invention also provides methods for treating chronic wounds using the scaffold and/or recombinant chimeric peptides.

3 Claims, 10 Drawing Sheets

Forward primer:
5'-CGG-AAT-TCA-ATG-AAG-ACC-CAA-AGG-GAT-GGC-3' (SEQ ID NO: 7)
Reverse primers:
5'-CG-GGA-TCC-TCA-ATA-AAA-CGT-CCC-AGT-CTC-TGA-ATC-CTG-GCA-CTT-GTC-GTC-ATC-GTC-TTT-GTA-GTC-GGA-CTC-TGT-CCT-GGG-TAC-AAG-3' with fibronectin derived anchor (SEQ ID NO: 8)
5'-CG-GGA-TCC-TCA-GGT-CCT-CAG-GGT-CTT-CTT-GGT- CTT-GTC-GTC-ATC-GTC-TTT-GTA-GTC-GGA-CTC-TGT-CCT-GGG-TAC-AAG-3' with collagenase derived anchor (SEQ ID NO: 9)

FIG. 6

5'-CGG-AAT-TCA-ATG-AAG-ACC-CAA-AGG-GAT-GGC-CAC-TCC-CTG-GGG-CGG-TGG-TCA-CTG-GTG-CTC-CTG-CTG-CTG-GGC-CTG-GTG-ATG-CCT-CTG-GCC-ATC-ATT-GCC-CAG-GTC-CTC-AGC-TAC-AAG-GAA-GCT-GTG-CTT-CGT-GCT-ATA-GAT-GGC-ATC-AAC-CAG-CGG-TCC-TCG-GAT-GCT-AAC-CTC-TAC-CGC-CTC-CTG-GAC-CTG-GAC-CCC-AGG-CCC-ACG-ATG-GAT-GGG-GAC-CCA-GAC-ACG-CCA-AAG-CCT-GTG-AGC-TTC-ACA-GTG-AAG-GAG-ACA-GTG-TGC-CCC-AGG-ACG-ACA-CAG-CAG-TCA-CCA-GAG-GAT-TGT-GAC-TTC-AAG-AAG-GAC-GGG-CTG-GTG-AAG-CGG-TGT-ATG-GGG-ACA-GTG-ACC-CTC-AAC-CAG-GCC-AGG-GGC-TCC-TTT-GAC-ATC-AGT-TGT-GAT-AAG-GAT-AAC-AAG-AGA-TTT-GCC☐CTG-CTG-GGT-GAT-TTC-TTC-CGG-AAA-TCT-AAA-GAG-AAG-ATT-GGC-AAA-GAG-TTT-AAA-AGA-ATT-GTC-CAG-AGA-ATC-AAG-GAT-TTT-TTG-CGG-AAT-CTT-GTA-CCC-AGG-ACA-GAG-TCC-GAC-TAC-AAA-GAC-GAT-GAC-GAC-AAG-ACC-AAG-AAG-ACC-CTG-AGG-ACC-TGA-GGA-TCC-CG-3' (SEQ ID NO: 10)

FIG. 7

RNSMKTQRDGHSLGRWSLVLLLLGLVMPLAIIAQVLSYKEAVLRAIDGINQRSSDANLY
RLLDLDPRPTMDGDPDTPKPVSFTVKETVCPRTTQQSPEDCDFKKDGLVKRCMGTVTL
NQARGSFDISKDNKRFALLGDFFRKSKEKIGKEFKRIVQRIKDFLRNLVPRTESDYKDDD
DKTKKTLRT*GS (SEQ ID NO: 11)

FIG. 8

5'-CGG-AAT-TCA-ATG-AAG-ACC-CAA-AGG-GAT-GGC-CAC-TCC-CTG-GGG-CGG-
TGG-TCA-CTG-GTG-CTC-CTG-CTG-CTG-GGC-CTG-GTG-ATG-CCT-CTG-GCC-ATC-
ATT-GCC-CAG-GTC-CTC-AGC-TAC-AAG-GAA-GCT-GTG-CTT-CGT-GCT-ATA-GAT-
GGC-ATC-AAC-CAG-CGG-TCC-TCG-GAT-GCT-AAC-CTC-TAC-CGC-CTC-CTG-GAC-
CTG-GAC-CCC-AGG-CCC-ACG-ATG-GAT-GGG-GAC-CCA-GAC-ACG-CCA-AAG-CCT-
GTG-AGC-TTC-ACA-GTG-AAG-GAG-ACA-GTG-TGC-CCC-AGG-ACG-ACA-CAG-CAG-
TCA-CCA-GAG-GAT-TGT-GAC-TTC-AAG-AAG-GAC-GGG-CTG-GTG-AAG-CGG-TGT-
ATG-GGG-ACA-GTG-ACC-CTC-AAC-CAG-GCC-AGG-GGC-TCC-TTT-GAC-ATC-AGT-
TGT-GAT-AAG-GAT-AAC-AAG-AGA-TTT-GCC☐CTG-CTG-GGT-GAT-TTC-TTC-CGG-
AAA-TCT-AAA-GAG-AAG-ATT-GGC-AAA-GAG-TTT-AAA-AGA-ATT-GTC-CAG-AGA-
ATC-AAG-GAT-TTT-TTG-CGG-AAT-CTT-GTA-CCC-AGG-ACA-GAG-TCC-GAC-TAC-
AAA-GAC-GAT-GAC-GAC-AAG-TGC-CAG-GAT-TCA-GAG-ACT-GGG-ACG-TTT-TAT-
TGA-GGA-TCC-CG-3' (SEQ ID NO: 12)

FIG. 9

RNSMKTQRDGHSLGRWSLVLLLLGLVMPLAIIAQVLSYKEAVLRAIDGINQRSSDANLY
RLLDLDPRPTMDGDPDTPKPVSFTVKETVCPRTTQQSPEDCDFKKDGLVKRCMGTVTL
NQARGSFDISKDNKRFALLGDFFRKSKEKIGKEFKRIVQRIKDFLRNLVPRTESDYKDDD
DKCQDSETGTFY*GS (SEQ ID NO: 13)

MATRIX SCAFFOLD WITH ANTIMICROBIAL ACTIVITY

CROSS-REFERENCE TO RELATED APPLICATIONS

This application claims priority to U.S. Provisional Application No. 61/664,386 filed Jun. 26, 2012 and entitled CELL-DERIVED MATRIX SCAFFOLD, the entire contents of which are incorporated herein by reference for all purposes.

BACKGROUND OF THE INVENTION

Skin is the body's main protective barrier against environmental insults. Significant wounds, caused by burns, physical trauma, surgery, and underlying pathologies, affect more than 35 million people annually in the United States. These full-thickness wounds lead to impaired tissue regeneration and loss of barrier function.

Scaffolds have been explored as a therapeutic method for regenerating skin at the wound site. Scaffolds provide a three-dimensional support through which cells can migrate, adhere, and regenerate a functional new tissue. Current scaffolds, however, are plagued by inadequate biocompatibility and biodegradability, mechanical and structural mismatch with the native tissue, and susceptibility to infection.

BRIEF SUMMARY OF THE INVENTION

In one aspect, the invention is generally directed to an antimicrobial extracellular matrix scaffold. More specifically, the invention is a scaffold comprising one or more extracellular matrix polymers and one or more chimeric peptides comprising one or more antimicrobial peptides and one or more extracellular matrix binding domains.

In certain embodiments of the invention, genetically modified human cells, i.e. transfected cells are used to generate a scaffold that is an entirely human, totally biological construct. Examples of cells that can be transfected to generate the scaffold of the invention include fibroblasts, keratinocytes, human lung carcinoma cells, smooth muscle cells, skeletal muscle cells, stem cells and combinations thereof. In a preferred embodiment, fibroblasts are genetically engineered to synthesize one or more recombinant antimicrobial peptides.

In certain embodiments of the invention, the cells can also be genetically modified to express additional factors that will impart novel activities to the scaffold, including, but not limited to, growth factors, extracellular matrix molecules, extracellular matrix-associated molecules, that promote enhanced angiogenesis, more rapid wound closure, functional tissue regeneration, tunable mechanical properties and infection treatment and prevention.

In certain embodiments, the genetically modified cells can be removed after producing a scaffold by a tailored decellularization protocol designed to maximize retention of scaffold structure and bioactivity. In still other embodiments, one or more chimeric peptides are added to previously produced extracellular matrix polymers, scaffolds or tissue substitutes (e.g. dermal substitutes) including those that are commercially available.

In another aspect, the invention is directed to the use of a cell-derived extracellular matrix scaffold for wound healing or tissue repair as well as infection control, including but not limited to chronic wounds. The matrix scaffold can be utilized as a cell-free material or can be seeded with cells.

In certain embodiments, the cell-derived extracellular matrix scaffold can be used for tissue repair and regeneration as applied to structural and/or functional restoration and healing of any tissue, e.g. dermal, periodontal, cardiovascular, orthopedic, craniofacial, musculoskeletal, endocrine, gastrointestinal, etc.

In certain embodiments, the one or more extracellular matrix polymers of the scaffold can be naturally occurring, artificial or combinations thereof. Naturally occurring polymers of the invention include collagen, fibronectin, laminin, elastin, hyaluronan, fibrin, gelatin, alginate, glycosaminoglycans or combinations thereof. Artificial polymers of the invention include poly-L-lactic acid, polyglycolic acid, polyurethane, polyethylene terephthalate, polytetrafluoroethylene, polycaprolactone or combinations thereof. In a preferred embodiment of the scaffold, the extracellular matrix polymer(s) is at least collagen.

In certain embodiments, the one or more antimicrobial peptides of the scaffold can be cathelicidins, defensins, chrysophsin, cecropins, cationic alpha-helical small molecule peptides or combinations thereof. In a preferred embodiments of the scaffold, the one or more antimicrobial peptide is MKTQRDGHSLGRWSLVLLLLGLVMPLAI-IAQVLSYKEAVLRAIDGINQRSSDANLYRLL DLD-PRPTMDGDPDTPKPVSFTVKETVCPRT-TQQSPEDCDFKKDGLVKRCMGTVTLNQA RGSFDISCDKDNKRFALLGDFFRK-SKEKIGKEFKRIVQRIKDFLRNLVPRTES (SEQ NO: 4).

In certain embodiments, the one or more extracellular matrix binding domains of the scaffold can be collagen binding domain, fibronectin binding domain, laminin binding domain, elastin binding domain, hyaluronan binding domain, fibrin binding domain, gelatin binding domain, alginate binding domain, glycosaminoglycan binding domain and combinations thereof, in preferred embodiments, the one or more extracellular matrix binding domains are collagen binding domains. In further preferred embodiments, the one or more extracellular matrix binding domains include TKKTLRT (SEQ ID NO: 5), CQDSETGTFY (SEQ ID NO: 6) or combinations thereof.

As used herein, the term "extracellular matrix binding domain(s)" refers to a conserved part of a given protein sequence having a 3D structure and that can evolve, function, and exist independently of the rest of the protein chain. The term "extracellular matrix binding domain(s) also refers to partial domains, i.e. fragments of the protein sequences including peptides (i.e. short amino acid sequences).

In certain embodiments, the one or more chimeric peptides of the scaffold is cathelicidin with collagen binding domains. In a preferred embodiment the one or more chimeric peptide is MKTQRDGHSLGRWSLVLLLLGLVMPLAI-IAQVLSYKEAVLRAIDGINQRSSDANLYRLL DLD-PRPTMDGDPDTPKPVSFTVKETVCPRT-TQQSPEDCDFKKDGLVKRCMGTVTLNQA RGSFDISCDKDNKRFALLGDFFRK-SKEKIGKEFKRIVQRIKDFLRNLVPRTES (SEQ ID NO: 4) and one or more of TKKTLRT (SEQ ID NO: 5) or CQDSETGTFY (SEQ ID NO: 6).

In another aspect, the invention is directed to chimeric peptides that are one or more antimicrobial peptides and one or more extracellular matrix binding domains. The chimeric peptides are recombinant antimicrobial peptide (e.g., cathelicidin, LL-37, or other antimicrobial peptide) that includes an extracellular matrix-binding domain (e.g., binding to collagen, or any extracellular matrix molecule). These recombinant peptides could be added exogenously as a coating onto extracellular matrix scaffolds or could be used as a therapeutic agent independent of the cell-derived extracellular matrix scaffold.

In certain embodiments, the chimeric peptide includes one or more antimicrobial peptides that can be cathelicidins, defensins, chrysophsin, cecropins, cationic alpha-helical small molecule peptides or combinations thereof. In a preferred embodiment, the antimicrobial peptide is cathelicidin. In a further preferred embodiment, the antimicrobial peptide is MKTQRDGHSLGRWSLVLLLLGLVMPLAIIAQVLSYKEAVLRAIDGINQRSSDANLYRLL DLDPRPTMDGDPDTPKPVSFTVKETVCPRT-TQQSPEDCDFKKDGLVKRCMGTVTLNQA RGSFDISCDKDNKRFALLGDFFRK-SKEKIGKEFKRIVQRIKDFLRNLVPRTES (SEQ ID NO: 4).

In certain embodiments, the chimeric peptide includes one or more extracellular matrix binding domains that can be collagen binding domain, fibronectin binding domain, laminin binding domain, elastin binding domain, hyaluronan binding domain, fibrin binding domain, gelatin binding domain, alginate binding domain, glycosaminoglycan binding domain or combinations thereof In a preferred embodiment, the one or more extracellular matrix binding domains are at least collagen binding domains. In a further preferred embodiment, the one or more extracellular matrix binding domains are TKKTLRT (SEQ ID NO: 5), CQDSETGTFY (SEQ ID NO: 6) or combinations thereof.

In certain embodiments, the chimeric peptides of the invention are cathelicidin with collagen binding domains. In a preferred embodiment the chimeric peptide is MKTQRDGHSLGRWSLVLLLLGLVMPLAIIAQVL-SYKEAVLRAIDGINQRSSDANLYRLL DLDPRPT-MDGDPDTPKPVSFTVKETVCPRTTQQSPEDCDFKKD-GLVKRCMGTVTLNQA RGSFDISCDKDNKRFALLGD-FFRKSKEKIGKEFKRIVQRIKDFLRNLVPRTES (SEQ ID NO: 4) and one or more of TKKTLRT (SEQ ID NO: 5) or CQDSETGTFY (SEQ ID NO: 6).

In certain embodiments of the invention, a bioengineered protein construct includes an antimicrobial domain from human cathelicidin, a natural antimicrobial peptide produced by keratinocytes, fused with one of two collagen-binding domains, one derived from fibronectin, the other derived from collagenase. The construct was designed to be expressed, synthesized, and secreted by the cells, and retained within the cell-derived extracellular matrix scaffold through its collagen binding domain. The collagen binding domain will allow retention of the antimicrobial peptide within the scaffold after the cells have been removed by the decellularization protocol.

In yet other aspects, the invention is directed to the recombinant antimicrobial, extracellular matrix-binding protein administered as the recombinant protein, as the recombinant gene, as transgenic cells overexpressing the protein, or the transgenic cells with or without an extracellular matrix scaffold.

BRIEF DESCRIPTION OF THE DRAWINGS

FIG. 6 is nucleotide sequences of PCR primers;

FIG. 7 is nucleotide sequence of cathelicidin with collagenase collagen binding domain (Col-CBD cathelicidin) construct;

FIG. 8 is protein sequence of Col-CBD cathelicidin;

FIG. 9 is nucleotide sequence of cathelicidin with fibronectin collagen binding domain (Fib-CBD cathelicidin) construct;

FIG. 10 is protein sequence of Fib-CBD cathelicidin;

DETAILED DESCRIPTION OF THE INVENTION

Extracellular matrix (ECM) is an appealing scaffold material that provides advantages over other natural and synthetic polymers currently used for skin therapies, including structural support in the wound bed with mechanical properties closely matching those of native tissue. Furthermore, ECM scaffolds provide growth factors and cytokines that mediate cellular migration, proliferation, and differentiation, thereby stimulating the natural wound healing response.

A primary deficiency that the invention addresses is the lack of antimicrobial activity, infection control in natural and synthetic tissue replacements. The production of both the extracellular matrix and the antimicrobial peptide by genetically modified cells represents a novel approach to producing a cell-derived, bioactive scaffold material. A unique feature of the antimicrobial peptide described herein is the incorporation of a collagen-binding domain, designed to facilitate tethering and localization to the extracellular matrix.

In order to address the limitations of current scaffolds a cell-derived ECM scaffold was designed that (1) provides the structural and mechanical properties of native extracellular matrix and (2) actively prevents wound infection. A stepwise design process towards producing a scaffold with antimicrobial activity and tailored mechanical properties in depicted in FIG. 1. To accomplish goal (1), human dermal fibroblasts were cultured into tissue sheets in media supplemented with ascorbic acid in order to increase collagen expression. To accomplish goal (2), the process is iterated and fibroblasts are genetically modified to produce an antimicrobial protein that adheres to the ECM. In the end, the modified ECM scaffold is isolated from the cell-derived tissue through decellularization.

Decellularization protocols were compared and collagen production, scaffold mechanical strength, and cathelicidin expression was assessed. Specifically, to produce a scaffold entirely from ECM, dermal fibroblasts were cultured into cell sheets and subjected to different decellularization techniques in order to optimize the removal of cellular debris. A gene construct was developed to modify fibroblasts to produce human cathelicidin (LL-37), an antimicrobial protein (AMP) that is naturally synthesized in the epidermis. The AMP was also designed to include the collagen-binding domain (CBD)

of either collagenase or fibronectin to allow fibroblasts to express, secrete, and tether the protein within the ECM.

Figure 1:
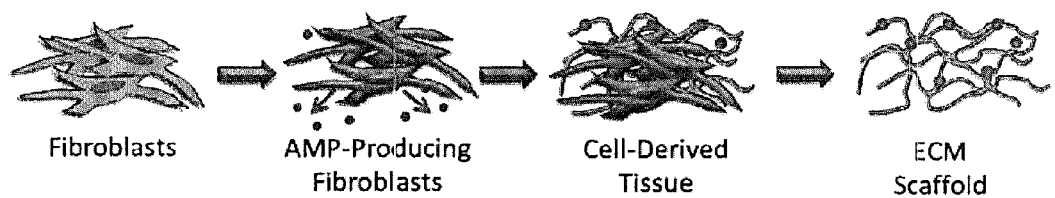
FIG. 1 is a diagrammatic representation of the process of making a cell-derived matrix scaffold.

The invention is further directed to methods for the treatment of chronic wounds with a cell derived ECM with antimicrobial properties as shown in FIG. 1. Treatment over time with antibiotics can cause bacterial resistant strains to form, but there is less bacterial resistance to antimicrobial polypeptides (AMPs) due to the mechanism with which they react with bacteria. This reduced resistance makes AMPs a beneficial addition to an ECM. The peptides also need to attach to an ECM to stay for the duration of therapy. Attachment to an ECM would allow for the wound to be washed and undergo the natural healing process without the loss of the antimicrobial property. The cell derived ECM will use cells that secrete the peptide at a therapeutically effective concentration.

AMPs are an innate part of the immunological cascade and can be found in mammals in the form of defensins and cathelicidins. The only human cathelicidin AMP to be isolated is the LL-37 cathelicidin peptide. The LL-37 peptide consists of a precursor region hCAP-18 (SEQ ID NO: 1 below), followed by the cathelin like domain that is present in all N-terminus ends of cathelicidins (SEQ ID NO: 2 below), and the AMP specific LL-37 region consisting of 37 amino acids (SEQ ID NO: 3 below). MKTQRDGHSLGRWSLVLLLLGLVM-PLAII (SEQ ID NO: 1); AQVLSYKEAVLRAI DGINQRSS-DANYLYRLLDLDPRPTMDGDPDTPKPVS-FTVKETVCPRTTQQSPEDCDFKKD GLVKRCMGTVTLNQARGSFDISCDK DNKRFA (SEQ ID NO: 2); LLGDFFRKSKEKIGKEFKRIVQRIKDFL-RNLVPRTES (SEQ ID NO: 3). The full sequence is MKTQRDGHSLGRWSLVLLLLGLVMPLAI-IAQVLSYKEAVLRAIDGINQRSSDANLYRLL DLD-PRPTMDGDPDTPKPVSFTVKETVCPRT-TQQSPEDCDFKKDGLVKRCMGTVTLNQA RGSFDISCDKDNKRFALLGDFFRK-SKEKIGKEFKRIVQRIKDFLRNVPRTES (SEQ ID NO: 4).

Figure 5:
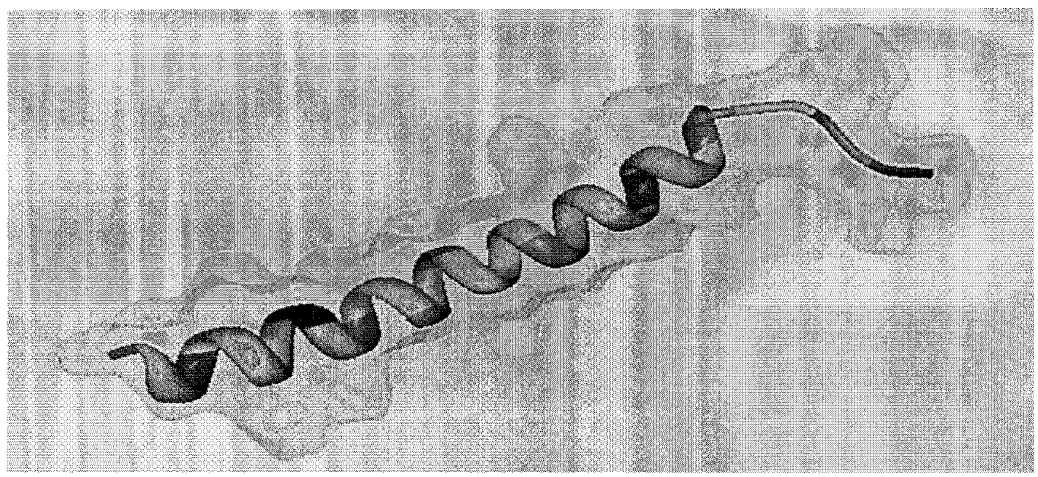
FIG. 5 is a drawing of the secondary structure of LL-37.
Figure 11:
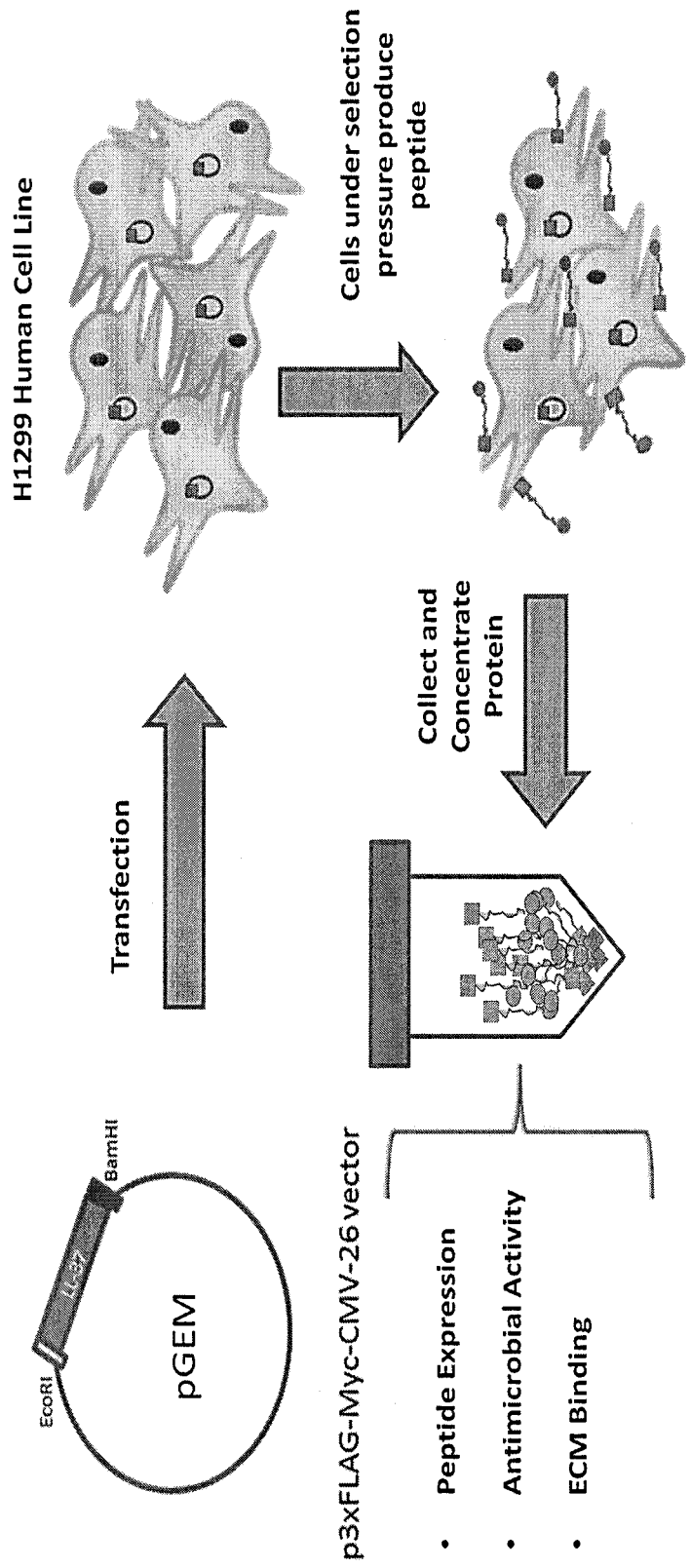
FIG. 11 is a diagrammatic representation of method of making a chimeric peptide of the current invention.

LL-37 has been found in beta cells, monocytes, mast cells, immature neutrophils and most importantly keratinocytes. FIG. 5 is an image of the LL-37 construct without the precursor hCAP-18 and the cathelin domain. LL-37 is located on the surface of the lipid bilayer in cells of the human body. It is an amphipathic alpha helix and is believed to target bacteria through cationic interactions to the anionic surface of bacteria. However, the exact mechanism of antimicrobial action is still not understood as 3D structures of the intact LL-37 bound to bacteria have never been produced.

Segmentation experiments have allowed for the antimicrobial activity of the LL-37 to be discovered. The residue KR-12 spanning amino acids 18-29 of the LL-37 holds the antimicrobial property for the antimicrobial polypeptide. Levels of LL-37 have been shown to increase after wound infliction to the skin barrier. Furthermore, potency of the AMP is affective to an array of bacteria, both gram negative and gram positive, leaving human cells unharmed. The present invention takes advantage of these properties of the Cathelicidin LL-37 AMP by adding it to an ECM for therapeutic use in treatment of wound infection and regeneration.

Figure 4:
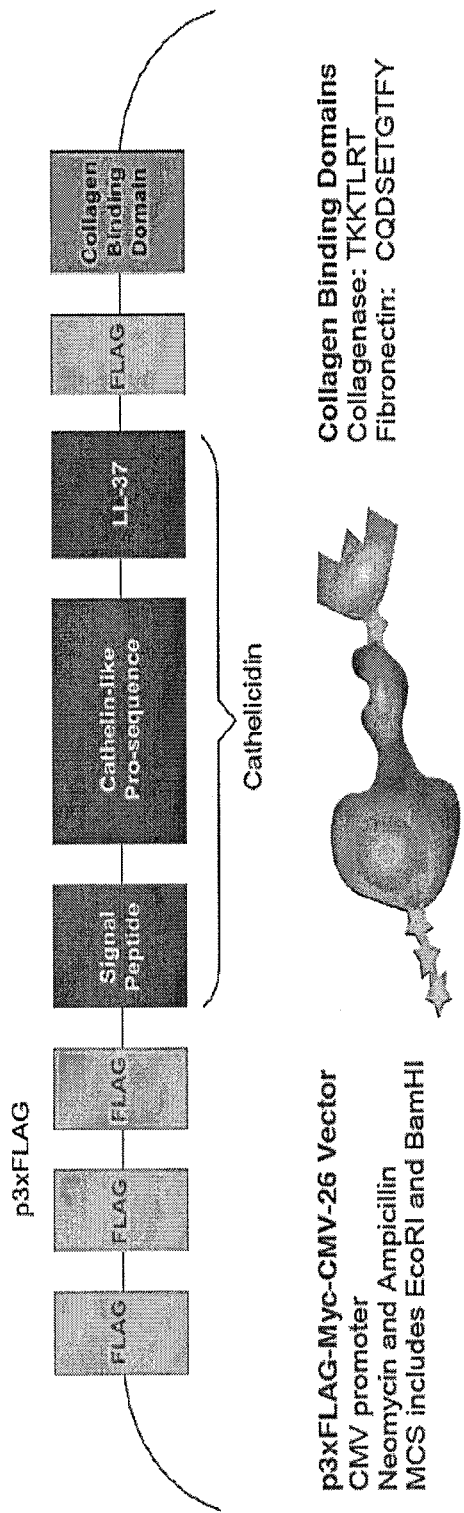
FIG. 4 is a diagrammatic representation of the gene design of recombinant collagen-binding cathelicidin.

In order to incorporate the LL-37 AMP in to an ECM, a recombinant was created to either anchor to a collagen surface. The collagen domains were chosen due to good affinity for their respective attachment sites. Furthermore, the flag-tag peptide was inserted before the binding domain at the C-terminus of cathelicidin so as to not hinder steric activity of the LL-37 AMP. FIG. 4 shows the recombinant cathelicidin LL-37 structure of the invention.

The 510 bp Cathelicidin gene was isolated from pANT7 cGST. It was then ligated into the pGEM vector to modify the gene with either a collagenase or fibronectin collagen binding domain (BD) (Col-CBD or Fib-CBD). This insert was transformed into E. coli and were selected and then sent for Sanger sequencing. Once the sequence was verified one more modification was made to the construct through the addition of the p3xFlags. This was done by ligation of the cathelicidin constructs in to the p3xFLAG-Mye-CMV-26 vector. E. coli were transformed and the colonies were selected for amplification and then purification of the plasmid. H1299 cells were transfected via effectene lipofection methods known in the art, due to their high efficiency of transformation. A GFP-Flag-Apoptin control vector was used to determine if transfection occurred. Results showed the GFP vector being expressed when viewed at 200× magnification with a fluorescence microscope.

The present invention provides a cell-derived ECM with the continuous production and secretion of the recombinant forms of human Cathelicidin LL-37. This invention is especially useful for the treatment of chronic dermal wounds, in particular those infected by multiple-drug-resistant strains of bacteria. The disclosure herein verifies the presence of the plasmid DNA insert, describes stably transfected recombinant Cathelicidin LL-37 in H1299 cells, and determines localization of the peptides. Further aspects contemplated as part of the present invention includes antimicrobial testing in solution, attachment testing to collagen films, and antimicrobial testing of the peptides after attachment.

Restriction-digestion with EcoRI and BamHI confirmed the presence of the insert in the pGEM vector. LL-37-fibronectin CBD and LL-37-collagenase CBD migrate at the predicted size on 1% agarose gel electrophoresis. H1299 cells were transfected to establish two stable cell lines, each expressing one recombinant peptide. The generation of these lines took approximately two weeks with passaging every 72 hours at this point no cell death was observed.

The localization of the peptide expression was investigated using Western blot analysis with anti-FLAG antibody. The expression was first observed in the whole cell lysate for both recombinant peptide forms, confirming that expression was occurring. Furthermore, expression also occurred in the soluble fraction for both peptide forms. For these samples, expression occurred at the expected molecular weight of 22. kDa.

Expression of the peptide was seen in the conditioned media for the collagenase collagen binding domain peptide form, but not for the fibronectin collagen binding domain peptide form. The concentration of the fibronectin form peptide appears to be below the sensitivity threshold of 2 ng of protein for the Western blot. To try to detect the peptide, conditioned media samples were concentrated via TCA precipitation. The Western blot analysis of the concentrated conditioned media shows expression for both recombinant peptide forms, but at a lower molecular weight than expected. This could be as a result of recombinant peptides being degraded by the TCA precipitation process, causing cleavage of approximately 5 kDa, or the recombinant peptides are being cleaved by the H1299 cells during the secretion process.

For chimeric peptide attachment, a collagen film was developed onto a silicone crystal surface using a QCM-d. The collagen film developed at low concentrations of collagen and was durable enough for the potential testing of attachment of the collagen-binding recombinant peptide. Chimeric peptides will be purified using affinity chromatography with an anti-FLAG resin using techniques known in the art. Purified chimeric peptides will be use for further ECM attachment testing and antimicrobial testing after attachment.

EXAMPLES

Example 1

Decellularization

A. Decellularization of Foreskins

Decellularization protocols were tested on foreskin samples as model demial tissue (foreskins collected from UMass Memorial University Hospital with IRB approval). Samples were prepared by scraping off fatty tissue and cutting the dermis to the size of 0.5 cm×0.25 cm.

1) Freeze-Thaw: Four samples were decellularized according to the protocol reported by Ngangan and McDevitt, 2009 (Biomaterials, 30(6):1143-49). The samples were immersed in liquid nitrogen for 2 min and then rotated in PBS at room temperature (RT) for 5 min. This cycle was repeated 3 times. Two of these samples were treated with DNase (1 mg/mL, 10 mM $MgCl_2$) for 15 min following all freeze-thaw (FT) cycles. One was fixed immediately after treatment, and one was fixed 8 hours after treatment.

2) Sodium Dodecyl Sulfate: Six samples were decellularized using sodium dodecyl sulfate (SDS) according to the protocol by Elder et al., 2009 (Biomaterials, 30(22)3749-56). Samples were immersed in 2% SDS and rotated at 37° C. for 1, 5, or 24 hrs. After treatment, the samples were rinsed 5 times in PBS for 10 min while rotating. Samples were fixed either immediately after the washes or after a 15 min treatment with DNase (1 mg/mL, 10 mM $MgCl_2$).

Analysis of Decellularization

Figure 2:
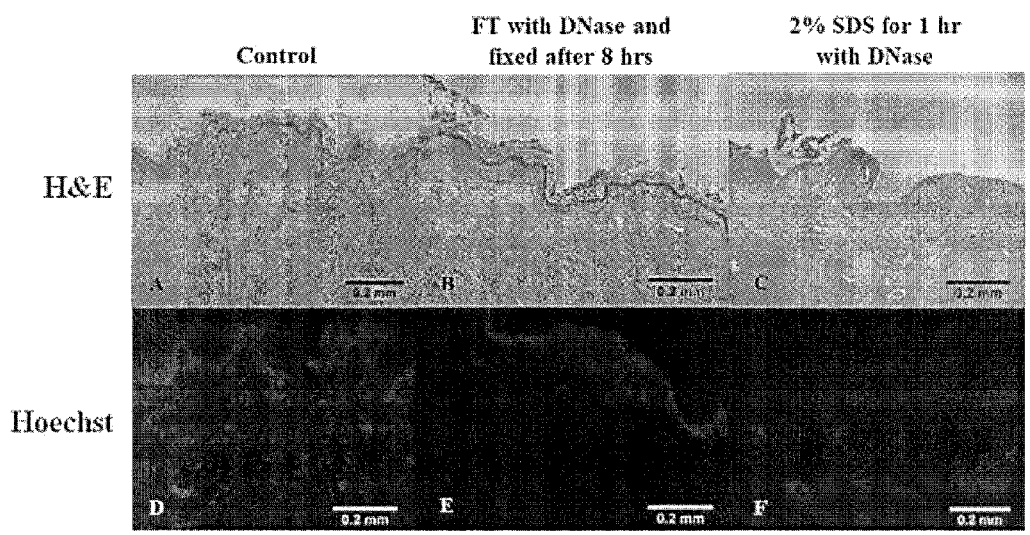
FIGS. 2A-F are photographs of H&E and Hoechst Staining of Decellularized Foreskins, (A) and (D): control tissues; (B) and (F): FT tissue with DNase and fixed after 8 hrs; (C) and (F): SDS for 1 hr with DNase.

Foreskin samples survived FT and SDS decellularization with minimally visible disruption to the architecture of the tissue. Histology revealed more extensive decellularization in samples treated with DNase as well as the FT samples that were fixed after 8 hrs (FIG. 2). Hoechst (FIG. 2D-F) identified the presence of genetic material and adjacent sections stained with H&E (FIG. 2A-C) confirmed the preservation of tissue structure.

FIG. 2D shows the presence of blue nuclei in the control tissue, as expected. FIG. 2F shows complete decellularization of the dermis and decellularization/loss of the epidermis, while FIG. 2E shows complete decellularization of the dermis and only minor decellularization of the epidermis.

B. Fibroblast Tissue Sheet Culture

Human neonatal fibroblasts were grown at 5% $CO_2$ in IMDM containing 10% FBS, penicillin/streptomycin, L-glutamine, and 25 mM HEPES. Fibroblasts were seeded at 100,000 cells/$cm^2$ on NIPAAM (poly(N-isopropylacrylamide)-coated UpCell™ 24-well plates (Thermo Fisher Scientific, Inc.) and cultured for 14 days. Tissues received 1 mL of IMDM containing 5% FBS with or without 50 μg/mL of L-ascorbic acid. Media was changed every 2 days. Tissues were cultured in ascorbic acid to increase collagen production.

C. Mechanical Testing of Tissues

Uniaxial tensile testing was performed by mounting tissue samples on an instron ELECTROPULS E1000 with custom grips and 50N load cell. Tissues were strained at 10 mm/min. Tensile testing was used to assess the contribution of ascorbic acid to ECM strength.

D. Histological Tissue Characterization

Hemotoxylin and Eosin (H&E) staining was used to observe tissue structure before and after decellularization. H&E stains nuclei blue, cytoplasm pink, and blood red. Hoechst was used to identify nuclei. Ficrosirius Red/Fast Green staining was used to identify collagen in the fibroblast sheets.

Fibroblast Tissue Sheet Characterization

Fibroblast tissue sheets were cultured for 14 days and remained adhered to the plate surface. Histological sections indicated collagen production (data not shown). During preliminary mechanical testing, samples cultured without ascorbic acid failed during testing preparation.

E. Antimicrobial Peptide Incorporation

The 510 bp human cathelicidin gene was isolated from pANT7 cGST using PCR, and modified to include the CBD of collagenase, TKKTLRT, or fibronectin, CQDSETGTFY. The PCR fragments were ligated into pGEM T-vector and the ligation products were isolated by E. coli transformation and blue-white ampicillin screening. Positive clones were isolated and analyzed by restriction mapping with EcoRI and BamHI. The fragments were then purified by Promega's SV Gel Clean-up kit and confirmed by sequence analysis. The final constructs were prepared by ligation into p3xFLAG. The ligation was verified by transformation into E. coli and subsequent restriction analysis. To test the expression of the constructs. H1299 lung carcinoma cells were transfected using Qiagen's Effectene lipofection protocol. The transfection was verified using an Apoptin-GFP-FLAG construct. The expression of the AMP was determined by Western blot analysis of cell lysates with an anti-FLAG antibody.

Antimicrobial Peptide Expression in H1299 Cells

Figure 3:
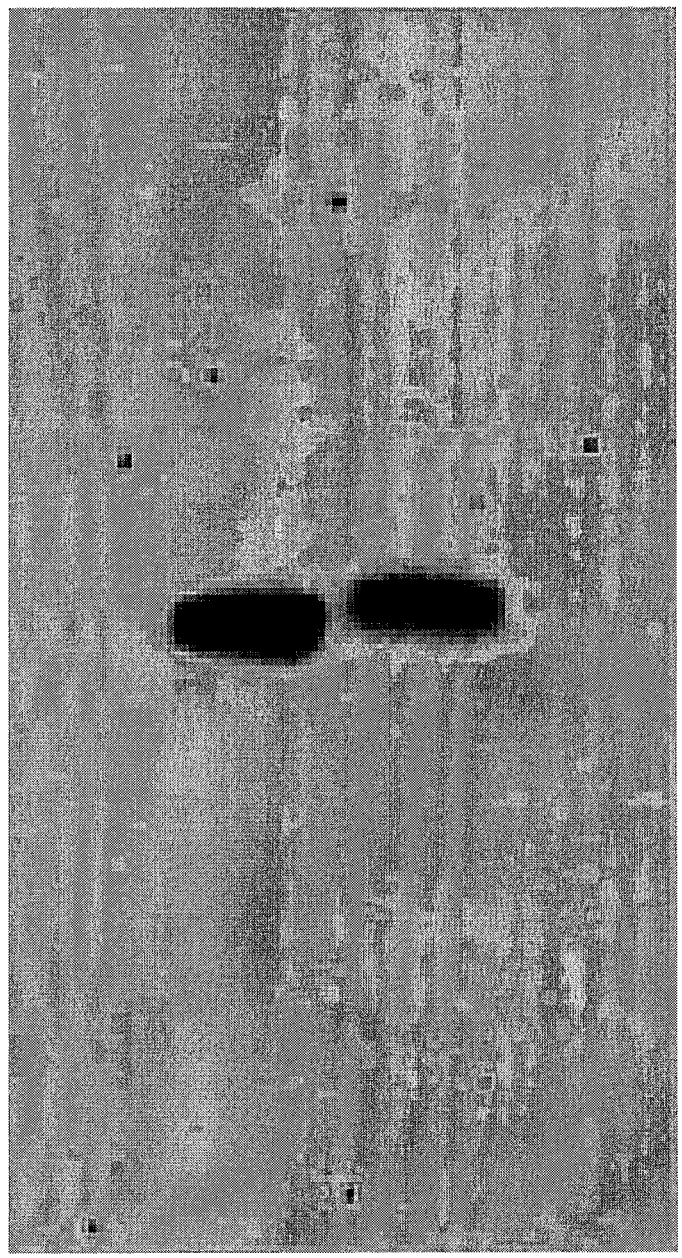
FIG. 3 is a Western Blot Showing Recombinant Cathelicidin Expression. (A) shows Cathelicidin-Collagenase CBD and (B) shows Cathelicidin-Fibronectin CBD.

The expression of the cathelicidin-CBD constructs was verified by Western blot. The products were probed with an anti-FLAG antibody against the flag sequences fused to cathelicidin. The bands confirm expression of both recombinant forms of cathelicidin (FIG. 3).

Towards achieving an ECM scaffold with tailored mechanical properties, it was qualitatively shown that cell sheets grown with ascorbic acid were stronger than those without ascorbic acid. Future mechanical testing will be performed to confirm the quantitative significance of ascorbic acid on mechanical strength. Additionally, analysis of decellularized foreskins revealed that SDS and freeze-thaw, both with DNase treatment, are efficient methods of removing cellular debris without significantly compromising the structure of the native dermis. Freeze-thaw will be explored further due to its reported retention of matrix components. Future experiments will determine how freeze-thaw affects the mechanical strength of the cell-derived ECM scaffold.

Example 2

Chimeric Peptide Production

The 510 bp cathelicidin insert was isolated and amplified from pANT7 cGST (DNASU Plasmid Repository, Clone ID HsCD00357894, GenBank Acc. No. 570277) using PCR. Primers were designed to include and incorporate the recombinant features onto the cathelicidin insert. One forward and two reverse primers (corresponding to each CBD) were ordered from Integrated DNA Technologies (IDT). The sequences of the three primers are shown in FIG. 6.

For PCR, the samples were prepared by combining 10 μL of Promega's GoTac Green Mastermix, 1 μL of the template (pANT7-cGST), 1 μl forward primer, 1 μL reverse primer, and ddH2O to 20 μL. PCR controls included a sample with no primers, and two with primers and no template (the two corresponding to each of the reverse primers). The PCR thermocycler (Bio-Rad, MyCycler) was set to 4 min at 90° C. (30 s at 95° C., 30 s at 55° C., 1 min at 72° C.)×30, 4 min at 72° C., and ∞ at 10° C. Agarose gel electrophoresis, pre-stained with Sybr green was used to verify the recombinant amplified cathelicidin fragments. The isolated fragments were subsequently purified with Promega's Wizard SV Gel and PCR Clean-up System.

Ligation into pGEM Vector. The purified PCR fragments were ligated into pGEM using Promega's T-vector system. The ligation reactions were set up to include 5 μL Ligation Buffer, 1 uL pGEM, 2 uL PCR fragment, 1 uL T4 DNA ligase, and filled to 10 uL with ddH2O. A positive control was prepared with control DNA, instead of the PCR fragments, and a negative control was prepared without DNA. The ligation reaction was run overnight at 4° C.

E. Coil Transformation, Screening, and pGEM Isolation. The pGEM vectors from the ligation reactions were used to transform chemically competent JM109 (Promega, >108 cfu/μg, Cat. No. L2001) E. coli cells. For each transformation, 50 μL of E. coli were transferred into a cold Eppendorf tube containing 2 μL of the ligation reaction. The mixture was mixed by tapping a tube on the benchtop. It was allowed to incubate on ice for 20 min, then heat shocked in a 42° C. waterbath for 60 s, before it was returned to ice for another 2 minutes. The E. coli then received 450 μL of prewarmed LB media and incubated at 37° C. under moderate shaking for 1 hour. Prewarmed LB agar Ampicillin plates were prepared with 20 μL of 50 mM X-Gal and 40 μL of 100 mM IPTG, spread on the surface of the agar. Sample plates were prepared in duplicate with 150 μL of transformed E. coli added to each. A plate of each the negative ligation and the positive ligation were prepared as controls. All of the plates were cultured overnight at 37° C. and then incubated at 4° C. for 6 hrs.

Blue-white colony screening was used to isolate positive (white) colonies and test for fragment incorporation into the vector. The pGEM vector includes the LacZ gene for 13-galactosidase (13-gal) with the multiple cloning site (MCS) positioned in the middle of the gene. The expression of 13-gal and the presence of X-gal, results in a blue bacterial phenotype. When the LacZ gene is interrupted by the insertion of a gene of interest (GOI), in this case cathelicidin, the 13-gal is not expressed, and thus the colony phenotype is white.

Individual colonies were screened by a miniprep protocol which included inoculating 3 mL of LB 1× AMP media and incubating it overnight at 37° C. Half of the culture was used to isolate the plasmid. The cells were pelleted by centrifugation at 12,000 rcf for 30 s, and the supernatant was aspirated. A resuspension solution was prepared with 50 mM Glucose, 25 mM TRIS-HCL and 10 mM EDTA at pH8, autoclaved and vacuum sterile filtered, Then 100 μL of ice-cold resuspension solution (~4° C.) was added to the pelleted cells. The cells were vortexed until fully resuspended. A cell lysis solution was freshly prepared with 100 μL NaOH (10N), 500 μL 10% SDS. and 4.4 mL of water and stored at room temperature until 200 μL was added to the resuspended cells, and each tube was inverted ten times and incubated on ice for 3 minutes. A third solution was prepared to precipitate the cellular debris (60 mL, 5M potassium acetate, 11.5 mL glacial acetic acid, and 28.5 mL $H_2O$, and stored at 4° C.) and 150 μL was added to the lysed cells. They were then vortexed in an inverted position at low speed for 10 s. The mixture was incubated on ice for 10 min, and then centrifuged at 12,000 g for 5 min. The 450 μL of supernatant was transferred to a fresh vial, and two volumes of 100% cold ethanol was added, mixed by vortex, and left to incubate on ice for 2 min. The DNA was pelleted by centrifugation at 12,000 ref for 5 min, and the supernatant ethanol was removed by pipette. The pellet was then rinsed with 1 mL of 70% ethanol and left to dry for 10 min at room temperature. After completely dry, the pellet was resuspended in 50 uL of 1×TE (10 mM Tris, 1 mM EDTA, pH 7.5).

Restriction Digest and Fragment Purification. Restriction digests were performed to isolate the recombinant cathelicidin inserts from the pGEM vector. Once a colony proved positive for the vector and insert, the DNA was isolated with a large scale plasmid isolation, using Promega's Midiprep Plasmid Isolation kit (Cat. No. A2492). The restriction reactions of the Midiprep DNA were conducted using 3 μL ligated DNA, 2 μL 10× Buffer E (Promega), 1 μL BamHI, 1 μL EcoRI, 1 μL RNAse A, and to 20 μL total with ddH2O. Controls were also run; one without BamHI, one without EcoRI, and one with neither restriction nuclease. Gel electrophoresis was performed to verify the restrictions. One positive restriction of each recombinant form of the cathelicidin insert (fib and col) was run again in triplicate. The isolated cathelicidin inserts were purified by Promega's SV Gel Clean-up kit (Cat. No. A9281) and protocol, then submitted for Sanger sequencing.

p3xFLAG Ligation, Transformation, and Verification. The two recombinant cathelicidin inserts were constructed by ligation into p3xFLAG-Myc-CMV-26 vector (Sigma Aldrich, Cat. No. E7283). The ligation reaction was prepared with 5 μL 10× T4 ligase buffer, 2 μL p3xFLAG, 3 μL purified DNA inserts, 1 μL T4 ligase, to a total of 10 μL with ddH2O. A negative control was prepared with no insert DNA. The ligations were incubated overnight at 4° C.

Transformations into JM109 E. coli were performed following the same protocol as for the pGEM transformations. Cells were plated on LB-AMP agar plates, and cultured overnight at 37° C. The colonies transformed with ligated p3xFLAG vector were selected by ampicillin resistance. The negative control, containing p3xFLAG with no insert, showed very few colonies, due to the improper ligation of the vector, resulting from the mismatching restricted ends (EcoRI and BamHI).

The colonies were screened for properly ligated p3xPLAG and insert using the miniprep protocol, followed by restriction analysis. Positive colonies were then cultured and their DNA was isolated using Promega's Midiprep kit. A restriction analysis of the final construct was done to verify the insertion of the recombinant cathelicidin inserts.

H1299 Transfection. Because of the low transfection efficiency of primary dermal fibroblast s, human lung carcinoma (H1299) cells were used as a model cell type to verify the design of the construct and its mammalian expression. The cells were seeded to attain 80% confluence after 24 hrs of culture. They were maintained with standard DMEM with 10% FBS on 6-well tissue culture plates (CellTreat, Cat. No. 229106) and incubated at 37° C. The cells were transfected with the two cathelicidin p3xFlag constructs using Qiagen's Effectene lipofection kit and protocol (Cat. No. 301425). A GFP-Flag-Apoptin control vector was used to verify the success of the transfection (Heilman, Teodoro and Green 2006). Each construct was transfected in duplicate.

Western Blot. Expression of the control CFP vector was assessed 24 hrs after transfection by examining the cells using a Zeiss Axiovert 40CFL inverted fluorescence microscope at 200×. To prepare cell lysates for Western blot analysis, each well was scraped after 2 washes with 1× PBS. The cell solution from each well (in 400 ul PBS) was centrifuged at 1500 rpm for 10 min. The supernatant was removed and the cell pellet was resuspended in 200 ul RIPA lysis buffer (50 mM Tris pH 7.6, 200 mM NaCl, 1% NP-40, 0.1% SDS, and 2 mM PMSF) and incubated on ice for 20 min. The suspension was then centrifuged at 5000 ref for 10 min, and the clarified lysate was transferred to a fresh vial. Lysates were stored at −20° C. until ready for Western analysis.

For the Western blot, a 16% SDS-polyacrylamide resolving gel was prepared with 5.3 mL 30% Acrylimide/0.8% Bis, 2.5 mL resolving buffer (1.5M Tris-HCL pH8.8), 0.1 mM 10% SDS, and 2.1 mL ddH2O. The polymerization was catalyzed with 50 µL 10% ammonium persulfate (APS) and 7 µL TEMED. The gel was poured using a Bio-rad Mini Gel apparatus. The stacking gel consisted of 0.65 mL 30% Acrylamide/0.8% Bis, 1.25 mL stacking gel buffer (0.5M Tris-HCL pH 6.8), 50 µL 10% SDS, and 3.05 mL ddH2O. The gel was polymerized with 25 µL 10% APS and 5 µL TEMED.

The Western samples were prepared with 20 µL of lysate and 5 µL of protein loading dye. The samples were denatured on a heating block at 95° C. for 5 min before loading them onto the gel. Invitrogen's Novex Sharp prestained ladder (Cat. No. LC5800) was used as the standard. The gel was run in a 1× Tris-Glycine pH 8.3 running buffer (0.3% tris, 1.44% glycine, 0.1% SDS), at 35 mAmps for 2 hr at a constant current.

The gel was transferred onto a nitrocellulose membrane, and run in a 1× Tris-Glycine (without SDS) transfer buffer containing 20% methanol, for 1 hr at 200 mAmps constant current. Immediately after the transfer, the membrane was blocked on a shaker at 4° C. overnight with 5% powdered milk in 1× Tris Buffered Saline Tween-20, pH 7.3 (TBS-T) (25 mM Tris-HCL, 137 mM NaCl, 2.7 µM KCl, to 1000 mL with ddH2O, and 0.5% tween-20).

The blocked membrane was washed 5 times for 5 min each time in TBS-T, then incubated with α-FLAG mAb M2 1/5000 (Sigma, Cat. No. F3165-.2MG) in TBS-T for 5 hrs at 4° C. and 1 hr at room temperature on an agitator. After the primary incubation, the membrane was washed 5 times for 5 min each in TBS-T. It was then incubated in goat α-mouse 1/10000 antibody (Sigma, Cat. No. A4416-.5ML) for 1 hr on an agitator at room temperature. It was then washed 5 times for 5 min each in TBS-T and then washed 2 times for 5 min in TBS (without Tween-20).

Promega's horseradish peroxidase chemiluminescence ECL reagents (Cat. No. W1001) was used for the detection of the secondary antibody on the membrane.

Cathelicidin isolation and recombinant modification by PCR. The 510 bp cathelicidin gene was isolated from pANT7 cGST using predesigned forward and reverse primers. Gel electrophoresis of the PCR fragments as well as the original vector confirms the isolation and construction of both recombinant forms of cathelicidin. The first lane is the DNA ladder, the second lane represents cathelicidin with the collagenase CBD (Col-CBD), while the third lane represents cathelicidin with the fibronectin CBD (Fib-CBD). The last lane is a sample of the pANT7 cGST vector. From the gel, the size of the recombinant fragments is approximately 600 bp, whereas the original vector is ~5000 bp. To compare, the expected sizes of the Col-GBD and Fib-CBD fragments were 575 bp and 584 bp. The expected size of the vector was ~5700 bp.

Cathelicidin-CBD in pGEM. After ligation into pGEM and subsequent transformation into E. coli, positive colonies showed a white phenotype. Both plates transformed with pGEM containing cathelicidin showed very few blue colonies, The positive and negative controls, containing pGEM ligated with a test fragment or no fragment respectively, showed mostly blue colonies.

Positive colonies were cultured and tested for the recombinant cathelicidin inserts by restriction digestion. All of the recombinant cathelicidin fragments ran at the expected size range of 500-600 bp.

Sequence Analysis of Cathelicidin-CBD. Both Col-CBD and Fib-CBD fragments were sent for Sanger sequencing to validate their consensus to the designed construct. The comparison shows 100% consensus for both of the fragments.

Cathelicidin-CBD in p3xFLAG. Both Col-CBD and Fib-CBD fragments were ligated into the p3xFLAG-Myc-CMV-26 vector to form the final two constructs. E. coli transformation was used to isolate the constructs and amplify them. All colonies had a white phenotype and were abundant in the plates transformed with the cathelicidin-CBD-p3xFLAG vectors. The negative control, containing p3xFLAG with no insert, showed very few colonies, due to the improper ligation of the vector.

Restriction analysis used to verify the presence of the recombinant cathelicidin inserts. Both recombinant fragments ran at approximately 600 bp, close to their expected size.

Transfection and Expression of Cathelicidin-CBD in H1299 cells. The transfection efficiency was monitored 24 hrs after the transfection, by checking the expression of GFP in the Apoptin-FLAG-GFP wells. The 200× fluorescence image could be observed indicating that GFP is being expressed, confirming the success of the transfection.

The expression of the recombinant cathelicidins was analyzed by Western blot probing for the incorporated FLAG epitope. The the expression of both Col-CBD and Fib-CBD in H1299 cells was confirmed. No bands are seen in the lower molecular weight range.

Example 3

Localization of Chimeric Peptide

Transformation of E. coli and Verification Cathelicidin Construct. The pGEM vector with the recombinant cathelicidin DNA insert was amplified by E. coli transformation. Transformations were carried out with 50 µL of chemically competent E. coli and 2 µL of the pGEM plasmid with DNA insert in a cold Eppendorf tube. This mixture was incubated on ice for 20 minutes, heat shocked at 42° C. in a water bath for 45 s, before it was returned to ice for another 2 minutes. The E. coli received 450 µL of prewarmed LB media and was incubated at 37° C. under shaking at 100 rpm for one hour. 50 µL of the transformed E. coli were plated on to Pre-warmed LB agar Ampicillin plates. These plates were incubated overnight at 37° C.

The following day individual colonies were selected and inoculated in 3 mL of LB with 100 µg/mL of Ampicillin media and incubated overnight at 37° C. with shaking at 190 rpm. Macherey and Nagel's Nucleospin plasmid purification protocol and kit (Cat. No. 740953) were used to isolate the plasmid. The 3 mL of E. coli were centrifuged at 11,000 ref for 30 minutes. The supernatant was removed and 250 µL of resuspension buffer A1 was used to resuspend the pellet. Then 250 µL of lysis buffer A2 was added to the tube and allowed to incubate at room temperature for five minutes. Then 300 µL of neutralization buffer A3 was added to the tube and then centrifuged at 11,000 ref for 10 minutes. A column was added to a NoLid Eppendorf tube and 750 µL of the supernatant was added to the column and centrifuged at 11,000 ref for 1 minute, 600 µL of wash buffer A4 (ethanol) was added and centrifuged at 11,000 ref for 1 minute. The flow through was discarded and the silica membrane of the column was dried by centrifuging at 11,000 ref for 2 minutes. The column was transferred to an Eppendorf tube with a top and 42 µL of water were added to the column and then centrifuged at 11,000 ref for 1 minute. The column was discarded and the flow through in the Eppendorf tube contained the purified plasmid. The concentration of this plasmid collected was determined via a Nanodrop meter to measure its optical density.

To verify that the cathelicidin DNA was located within the pGEM vector collected in the miniprep, a restriction digest with 5 μL plasmid DNA, 2 μL 10× Buffer #2, 0.5 μL BamHI, 0.5 μL EcoRI, 1 μL BSA, and 11 μL of ddH2O. The samples were mixed with the enzymes being added last. The samples were centrifuged for 10 s and incubated at 37° C. for one hour. An agarose gel electrophoresis (1%), pre-stained with 1 μL Ethidium Bromide, was run at 75V for 45 minutes. LL-37 fibronectin-CBD was expected to run at 584 bp and LL-37 collagenase-CBD at 575 bp.

Cell Culture, Transjection, and Stable Cell Line Formation of H1299 Cells Cell Culture. H1299 Cells were cultured in RPMI 1640 with 10% FBS. Cells were passaged every 72 hours or when 80% confluence was reached. During the splitting process cells and media were collected for testing for presence of protein of interest by Western blot analysis. Cells were rinsed with PBS prior to trypsinizing and placed in the incubator at 37° C. for one minute. Then, the plates were tapped gently to dislodge cells from the plate and examined under a microscope to ensure the cells had detached from the plates surface. The plate was then washed with fresh media and this media was collected in a conical tube. The tube was then centrifuged at 1000 ref for five minutes to pellet the cells. The media was aspirated off of the pellet and the cells resuspended in fresh media. At this point a cell count of the resuspended media was done using a hemocytometer. In a 60 mm plate approximately 150,000 cells were plated in order to achieve 80% confluence in 72 hours. However, the L,L-37 fibronectin-CBD producing H1299 cells divide at a faster rate than the LL-37 collagenase-CBD producing H1299 cells and thus, about 100,000 cells of the LL-37 fibronectin-CBD would be plated in order to achieve 80% confluence in 72 hours. If the pellet was resuspended in 5 mL of media this would equal about 330 μL of cell resuspension media being plated. Cells were incubated at 37° C., high humidity, 19% O2, and 5% CO2 for 72 hours.

Transfection. Plasmid DNA from the previous step was used to transfect H1299 human lung carcinoma cells. H1299 cells were cultured in RPMI 1640 with 10% FBS in six well plates until the cells reached 80% confluence at 37° C. Invitrogen's Lipofectamine (Cat. No. 18324) was the reagent used during the transfection. 4.5 μg of plasmid DNA were added in to 250 μL of serum free media in an Eppendorff tube. In another set of tubes 250 μL of serum free media was mixed with 10 μL of lipofectamine. This was done in duplicate. Both tubes were incubated at room temperature for five minutes. The contents of each tube were combined together and incubated at room temperature for 45 minutes. After 45 minutes the tube of combined solutions was added dropwise to the cells. Two wells received the LL-37 fibronectin-CBD vector in lipofectamine and two wells received the LL-37 collagenase-CBD vector in lipofectamine, two wells were given no vector as the control. The wells were incubated overnight at 37° C. Half of the wells were kept in order to be put under selection pressure using G418 to create a stable transfection. The other half, were used for Western blot analysis to confirm expression of protein of interest.

Stable Cell Line Generation. Invitrogen's G418 (Cat. No. 1013127) was used to kill cells that were not expressing the neomycin gene present in the recombinant peptide. 500 μg/ml of the G418 was added to the RPMI 11640 with 10% PBS media on the cells and allowed to incubate at 37° C., high humidity, 19% O2, and 5% CO2 for 72 hours before the media was changed. After one week the cells were transferred from the 6 well dishes to 60 mm dishes. Cells were passaged every three days in fresh media containing 500 μg/ml of the G418 until no cell death was present. At this point the G418 concentration was reduced to 100 μg/mL.

Localization of Cathelicidin Peptide. Protein expression and localization/secretion was determined by Western blot analysis. Whole cell lysate, soluble fraction, conditioned media and concentrated conditioned media were all tested for presence of protein of interest. Each sample was prepared in a different manner for Western blot analysis.

Sample Preparations. Conditioned media from untransfected cells was collected and used as a negative control.

Conditioned media from both fibronectin-CBD peptide transfected cells, and the collagenase-CBD peptide transfected cells, respectively was also collected and stored at 4° C. until used for Western blot analysis. 100μL, of each sample was suspended in 100 μL of 2× SDS-PAGE loading buffer and boiled for five minutes then stored at −20° C. until ready for analysis.

Trichloroacetic acid precipitation (TCA) protocol was followed in order to concentrate the conditioned media, 500 μL of TCA (22%) was added to 1,000 μL of condition media. This was incubated at 4° C. for 10 minutes. The mixture was centrifuged at 14,000 ref for five minutes. The supernatant was removed and the pellet was washed twice with 500 μL ice cold acetone and centrifuged at 14,000 ref for five minutes. The pellet was dried on a 95° C. heating block and 250 μL of 2× SDS-PAGE loading buffer was added to the dry pellet. The pellet was resuspended in the 2× buffer by breaking the pellet with the pipet tip and then suspending up and down several times. The solution was then boiled and stored at −20° C. until ready for analysis.

For the whole cell lysate, H1299 cells were trypsinized, washed with RPMI 1640 with 10% FBS media, centrifuged at 1,000 ref for 5 minutes. Media was aspirated and the pellet was resuspended in 1,000 μL of PBS and placed in an Ependorff tube. This was then centrifuged at 2,000 ref for 10 minutes. The PBS was aspirated and the cells were suspended in 75 μL of 2× SDS-PAGE loading buffer. The samples were then sonicated with the Ultrasonic Cell Disrupter for twenty pulses (Missonix XL-2000 series at power 3). The tubes were boiled for five minutes then stored at −20° C. until ready for analysis.

The soluble fraction samples were prepared by taking 200 μL of the whole cells suspended in lysis buffer and sonicating the cells with the Ultrasonic Cell Disrupter for twenty pulses at power 3. This was then centrifuged at 14,000 ref for 15 minutes at 4° C. 100 μL of the soluble media was then transferred in to 100 μL of 2× SDS-PAGE loading buffer and boded for five minutes before being stored at −20° C. before western blot analysis.

SDS-PAGE gel electrophoresis and Immunoblotting. Western blot analysis was carried out using a 15% polyacrylamide resolving gel. The gel was poured using a Bio-rad MiniProtean Gel apparatus. Samples were denatured by boiling in 2× SDS-PAGE loading buffer for 5 minutes before loading. Different amounts of each sample (Table 2) were added per wells. 3 μL of Fermenta's Page Ruler Prestained Protein ladder (Cat. No. SM0671) was used as the standard.

The gel was run in a 1× Tris-Glycine pH 8.3 buffer at 160V for 60 minutes with a constant current. After running, the gel was transferred to a nitrocellulose membrane and run in a 1× Tris-Glycine transfer buffer (without SDS) containing 20% methanol for 1 hour at 100V constant current. After transfer, the membrane was immediately put on a shaker at room temperature for an hour in 5% non-fat dry milk in 1× Tris buffered saline Tween-20, pH 7.3. After, the membrane was incubated with anti-FLAG mAb M2 at 1/5000 dilution (Sigma, Cat. No. F3165-.2MG) in TBS-T overnight at 4° C. on a shaker. The membrane was washed 3 times for 10 minutes each in TBS-T. It was then incubated in rabbit anti-mouse at 1/5000 dilution (Abcam Cat. No. ab6729) for 1 hour on an agitator at room temperature. Then 3 washes for 10 minutes were applied again in TBS-T. Promega's Alkaline Phosphatase Western Blue Reagent (Cat. No. S3841) was used to visualize the bands on the membrane.

Determination of Protein Concentration in Samples Bradford Assay. Whole cell lysate and soluble fraction were tested for total protein concentration. The whole cell lysate was prepared by resuspending the cell pellet in 200 µL of a low detergent RIPA buffer and sonicating the pellet with the Ultrasonic Cell Disrupter for twenty pulses at power 3. Samples were kept on ice until ready for analysis. For the soluble fraction samples were prepared by taking 200 µL it of the whole cells suspended in RIPA buffer and sonicating the cells with the Ultrasonic Cell Disrupter for twenty pulses at power 3. This was then centrifuged at 14,000 ref for 15 minutes at 4° C. The supernatant was transferred to another Eppendorf tube and kept on ice until testing occurred.

In a 96 well plate 10 µL of low detergent RIPA buffer was put in to each well of the 96 well plate. Then 10 µL of BSA was added to the first well and serial diluted down the column dividing the concentration by a factor of two each time. This served as the control. In the other wells 10 µL of sample was added to the first row and serial pipetted down the column increasing the dilution factor by two each time. 190 µL of Thermo Scientific's Coomassie Bradford reagent (Cat. No. 23236) was added to each well as the colorimetric standard. Table 3 shows the dilutions layout for the 96 well plate. The optical density of the plate wells was measured through an automatic plate reader.

Collagen Film Development in a Quartz Crystal Micrograph with Dissipation Monitoring (QCM-d). The QCM-d was prepared using a washing procedure as follows: 10 mL of DI water, 0.01M SDS, and 10% ethanol were flowed through the chambers at 0.3 mL/min. The crystals were then removed from the chambers, dried off using a high flow of Nitrogen gas, and plasma etched. Afterwards they were placed back into the QCM-d. PBS was then flowed through at 0.1 mL/min until a stable baseline reading was achieved. After 5 minutes of stable baseline reading. 10 mL of collagen at a concentration of 0.5 mg/mL was flowed through the chambers at a flow rate of 0.1 mL/min. After the collagen flow, PBS was flowed at 0.1 mL/min to test the durability of the film that had attached to the crystals. After 3 hours, the film stabilized again and the flow rate of PBS was increased to 0.3 mL/min to test the resistance to shear forces.

Figure 12:
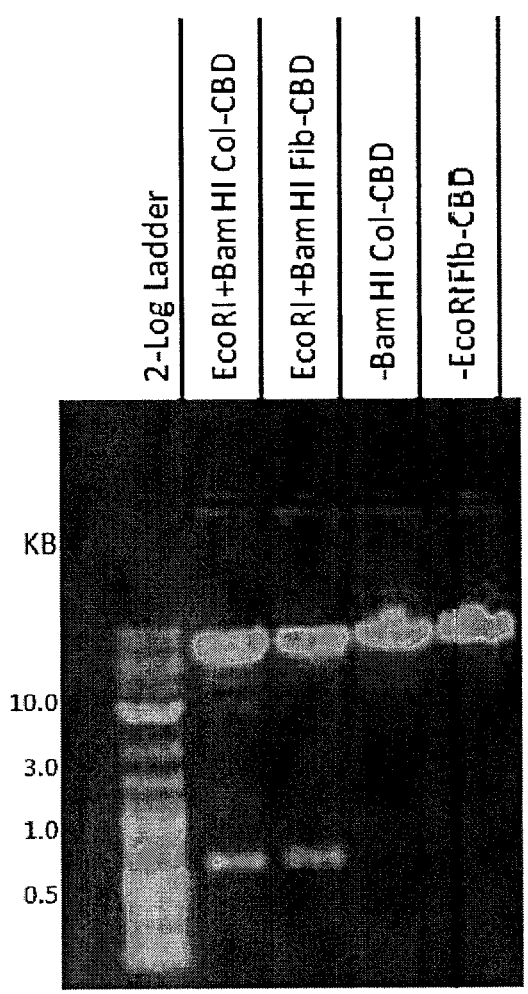
FIG. 12 is photograph of a stained agarose gel showing restriction digestion of pGEM vector with plasmid DNA inserts of the invention.

Verification of the Cathelicidin Construct Plasmid DNA. Agarose gel electrophoresis analysis of the restriction digest with EcoRI and bamHI, shows presence of LL-3 Collagenase-CBD and LL-37 Fibronectin-CBD in the pGEM vector (FIG. 12). Data shows that the digested samples have fragments produced at approximately 600 base pairs. The predicted size of the LL-37 DNA is 575 and 584 base pairs for collagenase collagen binding domain and fibronectin collagen binding domain respectively.

Stable transfection. Initially, approximately 300,000 cells were plated after transfection in to the six well dish for the fibronectin-CBD Cathelicidin H1299 cells, collagenase-CBD Cathelicidin H1299 cells, and the untransfected H1299 cells. Half of the cultures were used in Western blot analysis for expression and the other half were put under selection pressure with 500 µg/mL of G418. After six days all of the cells in the untransfected H1299 cell culture had died in the six well dish. After six days, the fibronectin-CBD Cathelicidin H1299 cells were at 80% confluence and the collagenase-CBD Cathelicidin H1299 cells were at 65% confluence. All cells were collected and the cells were moved to 60 mm dishes. Cells were split twice more after 72 hours each until no cell death appeared in the 60 mm dishes and then they were passaged to a 10 cm dish. Cells were allowed to grow for six days and the media was changed every 72 hours. At this point stocks were frozen in liquid nitrogen. The cells were moved back to a 60 mm dish in order to continue collection of conditioned media and the G418 concentration was reduced to 100 µg/mL. Cells were split for three more weeks every 72 hours until the cell lines were terminated.

Figure 13:
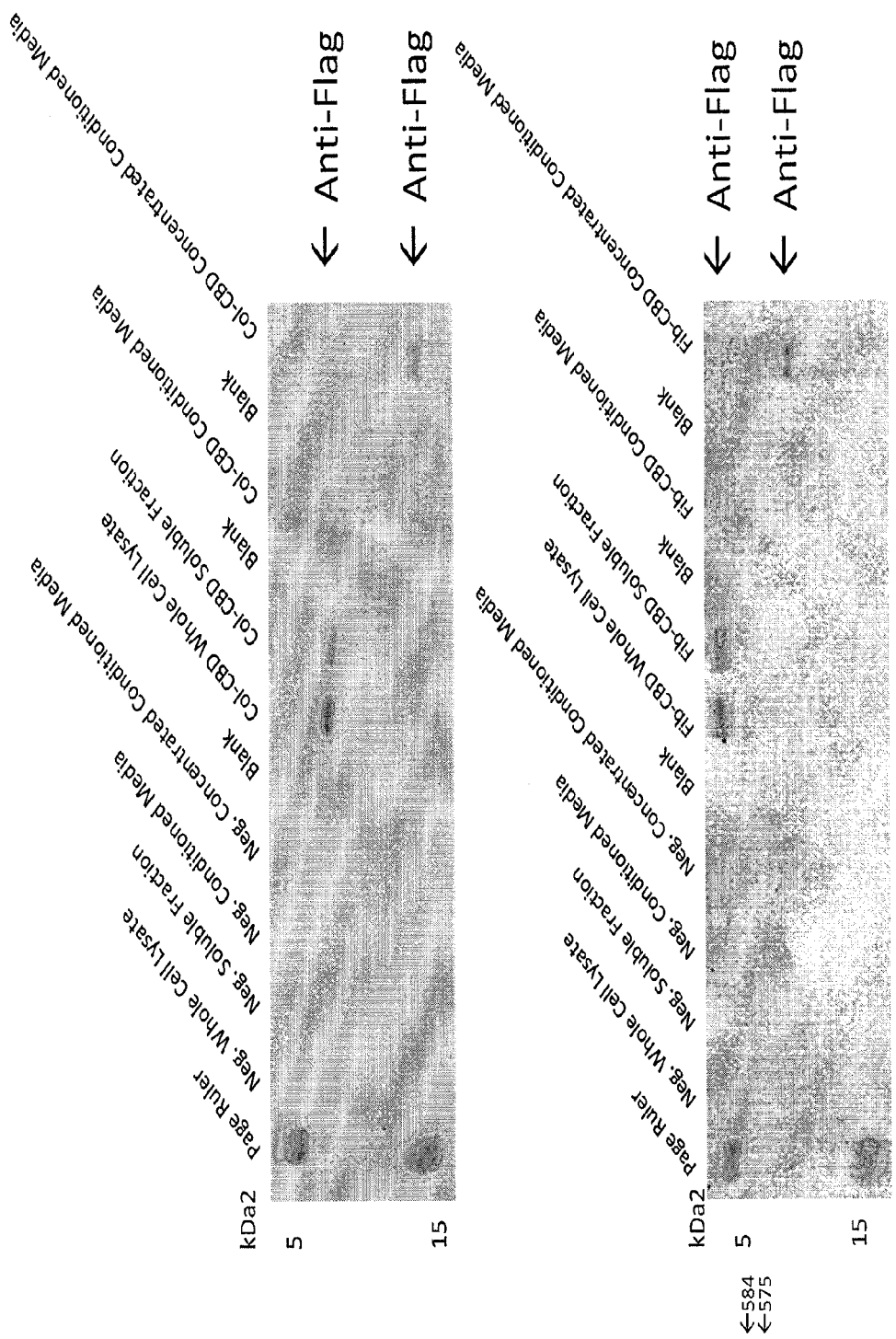
FIG. 13 is photographs of Western Blot results: top panel is Col-CBD cathelicidin isolated from transfected H1299 cells and bottom panel is Fib-CBD cathelicidin isolated from transfected H1299 cells.

Western Blot Analysis of Transfected Cells. In order to see if the transfected H1299 cells were expressing the recombinant Cathelicidin peptide, a Western Hot analysis was run. Western blot analysis allows for the visualization of the expression of the peptide. Taking samples from different aspects of the cell culture such as the conditioned media, the whole cell lysate and the soluble fraction of the whole cell lysate also allowed for a determination of where the peptide was expressing strongest. Predicted molecular weight of the protein by Western Hot was expected at approximately 22 kDa. FIG. 13a shows the Western blot of the collagenase collagen binding domain Cathelicidin transfected H1299 cells expressing the peptide in the whole cell lysate, soluble fraction, and conditioned media. Furthermore, the concentrated conditioned media shows expression of the peptide however; the expression is at a lower molecular weight. FIG. 13b shows the Western blot results from the fibronectin collagen binding domain Cathelicidin transfected H1299 cells. The peptide is expressed in both the whole cell lysate and soluble fraction. However, unlike the collagenase collagen binding domain Cathelicidin, the concentration of peptide in the conditioned media for the fibronectin collagen binding domain was below the sensitivity of the Western blot at 2 ng and no expression was seen. However, peptide is being secreted as the concentrated conditioned media sample shows expression. Again, this expression is at a lower molecular weight than the peptide being expressed by the whole cell and soluble fraction. For both Western blots there was no expression in the untransfected H1299 cells.

Figure 14:
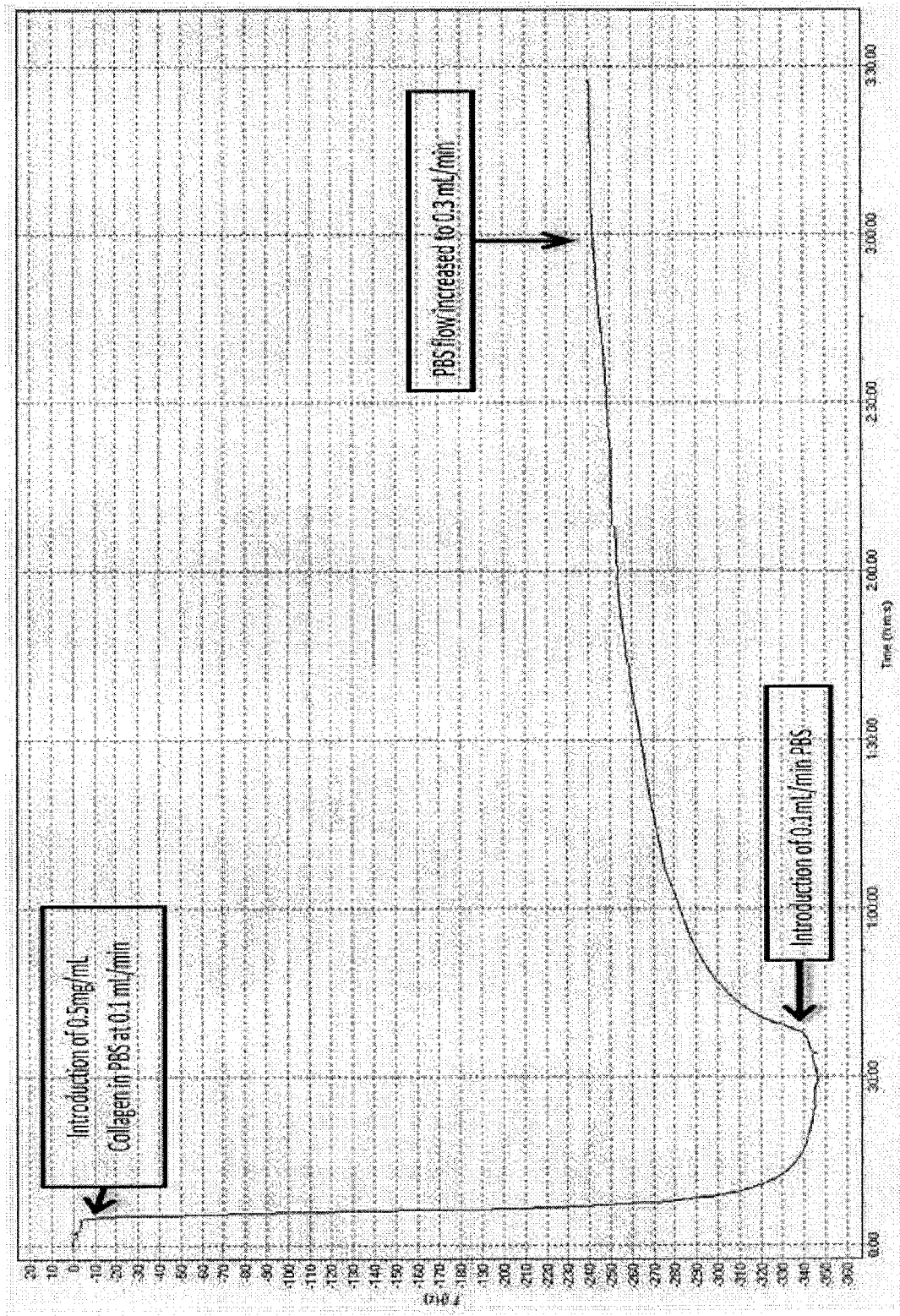
FIG. 14 is a graph showing collagen film development.

Collagen Film Development in QCM-d. A collagen film was deposited onto the QCM-d crystal surfaces and tested to observe whether a stable film could be developed, and if so the resilience of the film. Results are shown in FIG. 14, FIG. 14: Collagen film development in QCM☐d. Vertical Axis in Hz differential, horizontal axis is time. Collagen film rapidly deposited, degraded slightly over three hours of PBS flow, and then stabilized.

Quickly after the collagen solution begins flowing through the chambers, a film begins to attach to the crystals. When PBS was flowed through the chambers, the collagen film degraded somewhat over a 3 hour period, and then stabilized. When the flow rate of PBS was tripled, no further loss of film was observed. This suggests the film is resilient to some shear strain and reliable enough for further attachment testing with the purified recombinant peptides.

All publications cited herein are hereby incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A chimeric peptide comprising MKTQRDGHSLGRWSLVLLLLGLVMPLAIIAQVLSYKEAVLRAIDGINQRSSDANLYRLLDLDPRPTMDGDPDTPKPVSFTVKETVCPRTTQQSPEDCDFKKDGLVKRCMGTVTLNQARGSFDISCDKDNKRFALLGDFFRKSKEKIGKEFKRIVQRIKDFLRNLVPRTES (SEQ ID NO: 4) and a collagen binding domain selected from the group consisting of TKKTLRT (SEQ ID NO: 5) and CQDSETGTFY (SEQ ID NO: 6), attached to the C-terminal end of SEQ ID NO: 4 via a linker sequence comprising five aspartic acid residues, two lysine residues and a tyrosine residue.

2. The chimeric peptide of claim 1, wherein the collagen binding domain is SEQ ID NO: 5.

3. The chimeric peptide of claim 1, wherein the collagen binding domain is SEQ ID NO: 6.

* * * * *

SEQUENCE LISTING

<160> NUMBER OF SEQ ID NOS: 13

<210> SEQ ID NO 1
<211> LENGTH: 29
<212> TYPE: PRT
<213> ORGANISM: Homo sapiens

<400> SEQUENCE: 1

Met Lys Thr Gln Arg Asp Gly His Ser Leu Gly Arg Trp Ser Leu Val
1               5                   10                  15

Leu Leu Leu Leu Gly Leu Val Met Pro Leu Ala Ile Ile
            20                  25

<210> SEQ ID NO 2
<211> LENGTH: 104
<212> TYPE: PRT
<213> ORGANISM: Homo sapiens

<400> SEQUENCE: 2

Ala Gln Val Leu Ser Tyr Lys Glu Ala Val Leu Arg Ala Ile Asp Gly
1               5                   10                  15

Ile Asn Gln Arg Ser Ser Asp Ala Asn Leu Tyr Arg Leu Leu Asp Leu
            20                  25                  30

Asp Pro Arg Pro Thr Met Asp Gly Asp Pro Asp Thr Pro Lys Pro Val
        35                  40                  45

Ser Phe Thr Val Lys Glu Thr Val Cys Pro Arg Thr Thr Gln Gln Ser
    50                  55                  60

Pro Glu Asp Cys Asp Phe Lys Lys Asp Gly Leu Val Lys Arg Cys Met
65                  70                  75                  80

Gly Thr Val Thr Leu Asn Gln Ala Arg Gly Ser Phe Asp Ile Ser Cys
                85                  90                  95

Asp Lys Asp Asn Lys Arg Phe Ala
            100

<210> SEQ ID NO 3
<211> LENGTH: 37
<212> TYPE: PRT
<213> ORGANISM: Homo sapiens

<400> SEQUENCE: 3

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 4
<211> LENGTH: 170
<212> TYPE: PRT
<213> ORGANISM: Homo sapiens

<400> SEQUENCE: 4

Met Lys Thr Gln Arg Asp Gly His Ser Leu Gly Arg Trp Ser Leu Val
1               5                   10                  15

Leu Leu Leu Leu Gly Leu Val Met Pro Leu Ala Ile Ile Ala Gln Val
            20                  25                  30

Leu Ser Tyr Lys Glu Ala Val Leu Arg Ala Ile Asp Gly Ile Asn Gln
        35                  40                  45

```
Arg Ser Ser Asp Ala Asn Leu Tyr Arg Leu Leu Asp Leu Asp Pro Arg
        50                  55                  60

Pro Thr Met Asp Gly Asp Pro Asp Thr Pro Lys Pro Val Ser Phe Thr
 65                  70                  75                  80

Val Lys Glu Thr Val Cys Pro Arg Thr Thr Gln Gln Ser Pro Glu Asp
                 85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125

Asn Lys Arg Phe Ala Leu Leu Gly Asp Phe Arg Lys Ser Lys Glu
    130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170

<210> SEQ ID NO 5
<211> LENGTH: 7
<212> TYPE: PRT
<213> ORGANISM: Homo sapiens

<400> SEQUENCE: 5

Thr Lys Lys Thr Leu Arg Thr
 1               5

<210> SEQ ID NO 6
<211> LENGTH: 10
<212> TYPE: PRT
<213> ORGANISM: Homo sapiens

<400> SEQUENCE: 6

Cys Gln Asp Ser Glu Thr Gly Thr Phe Tyr
 1               5                  10

<210> SEQ ID NO 7
<211> LENGTH: 30
<212> TYPE: DNA
<213> ORGANISM: Homo sapiens

<400> SEQUENCE: 7
cggaattcaa tgaagaccca aagggatggc                              30

<210> SEQ ID NO 8
<211> LENGTH: 86
<212> TYPE: DNA
<213> ORGANISM: Homo sapiens
<220> FEATURE:
<221> NAME/KEY: misc_feature
<223> OTHER INFORMATION: with fibronectin derived anchor

<400> SEQUENCE: 8
cgggatcctc aataaaacgt cccagtctct gaatcctggc acttgtcgtc atcgtctttg   60
tagtcggact ctgtcctggg tacaag                                       86

<210> SEQ ID NO 9
<211> LENGTH: 77
<212> TYPE: DNA
<213> ORGANISM: Homo sapiens
<220> FEATURE:
<221> NAME/KEY: misc_feature
<223> OTHER INFORMATION: with collagenase derived anchor
```

<400> SEQUENCE: 9

```
cgggatcctc aggtcctcag ggtcttcttg gtcttgtcgt catcgtcttt gtagtcggac    60
tctgtcctgg gtacaag                                                  77
```

<210> SEQ ID NO 10
<211> LENGTH: 575
<212> TYPE: DNA
<213> ORGANISM: Homo sapiens

<400> SEQUENCE: 10

```
cggaattcaa tgaagaccca aagggatggc cactccctgg ggcggtggtc actggtgctc    60
ctgctgctgg gcctggtgat gcctctggcc atcattgccc aggtcctcag ctacaaggaa   120
gctgtgcttc gtgctataga tggcatcaac cagcggtcct cggatgctaa cctctaccgc   180
ctcctggacc tggaccccag gcccacgatg gatggggacc cagacacgcc aaagcctgtg   240
agcttcacag tgaaggagac agtgtgcccc aggacgacac agcagtcacc agaggattgt   300
gacttcaaga aggacgggct ggtgaagcgg tgtatgggga cagtgaccct caaccaggcc   360
aggggctcct ttgacatcag ttgtgataag gataacaaga gatttgccct gctgggtgat   420
ttcttccgga aatctaaaga gaagattggc aaagagttta aaagaattgt ccagagaatc   480 aaggatttt tgcggaatct tgtacccagg acagagtccg actacaaaga cgatgacgac   540
aagaccaaga gaccctgag gacctgagga tcccg                               575
```

<210> SEQ ID NO 11
<211> LENGTH: 188
<212> TYPE: PRT
<213> ORGANISM: Homo sapiens

<400> SEQUENCE: 11

```
Arg Asn Ser Met Lys Thr Gln Arg Asp Gly His Ser Leu Gly Arg Trp
1               5                   10                  15

Ser Leu Val Leu Leu Leu Gly Leu Val Met Pro Leu Ala Ile Ile
            20                  25                  30

Ala Gln Val Leu Ser Tyr Lys Glu Ala Val Leu Arg Ala Ile Asp Gly
        35                  40                  45

Ile Asn Gln Arg Ser Ser Asp Ala Asn Leu Tyr Arg Leu Leu Asp Leu
    50                  55                  60

Asp Pro Arg Pro Thr Met Asp Gly Asp Pro Asp Thr Pro Lys Pro Val
65                  70                  75                  80

Ser Phe Thr Val Lys Glu Thr Val Cys Pro Arg Thr Thr Gln Gln Ser
                85                  90                  95

Pro Glu Asp Cys Asp Phe Lys Lys Asp Gly Leu Val Lys Arg Cys Met
            100                 105                 110

Gly Thr Val Thr Leu Asn Gln Ala Arg Gly Ser Phe Asp Ile Ser Lys
        115                 120                 125

Asp Asn Lys Arg Phe Ala Leu Leu Gly Asp Phe Phe Arg Lys Ser Lys
    130                 135                 140

Glu Lys Ile Gly Lys Glu Phe Lys Arg Ile Val Gln Arg Ile Lys Asp
145                 150                 155                 160

Phe Leu Arg Asn Leu Val Pro Arg Thr Glu Ser Asp Tyr Lys Asp Asp
                165                 170                 175

Asp Asp Lys Thr Lys Lys Thr Leu Arg Thr Gly Ser
            180                 185
```

<210> SEQ ID NO 12
<211> LENGTH: 584
<212> TYPE: DNA
<213> ORGANISM: Homo sapiens

<400> SEQUENCE: 12

```
cggaattcaa tgaagaccca aagggatggc cactccctgg ggcggtggtc actggtgctc      60
ctgctgctgg gcctggtgat gcctctggcc atcattgccc aggtcctcag ctacaaggaa     120
gctgtgcttc gtgctataga tggcatcaac cagcggtcct cggatgctaa cctctaccgc     180
ctcctggacc tggaccccag gcccacgatg gatgggacc cagacacgcc aaagcctgtg      240
agcttcacag tgaaggagac agtgtgcccc aggacgacac agcagtcacc agaggattgt     300
gacttcaaga aggacgggct ggtgaagcgg tgtatgggga cagtgaccct caaccaggcc     360
aggggctcct ttgacatcag ttgtgataag gataacaaga gatttgccct gctgggtgat     420
ttcttccgga atctaaaga gaagattggc aaagagttta aagaattgt ccagagaatc       480
aaggattttt tgcggaatct tgtacccagg acagagtccg actacaaaga cgatgacgac     540
aagtgccagg attcagagac tgggacgttt tattgaggat cccg                      584
```

<210> SEQ ID NO 13
<211> LENGTH: 191
<212> TYPE: PRT
<213> ORGANISM: Homo sapiens

<400> SEQUENCE: 13

```
Arg Asn Ser Met Lys Thr Gln Arg Asp Gly His Ser Leu Gly Arg Trp
1               5                   10                  15

Ser Leu Val Leu Leu Leu Gly Leu Val Met Pro Leu Ala Ile Ile
            20                  25                  30

Ala Gln Val Leu Ser Tyr Lys Glu Ala Val Leu Arg Ala Ile Asp Gly
        35                  40                  45

Ile Asn Gln Arg Ser Ser Asp Ala Asn Leu Tyr Arg Leu Leu Asp Leu
    50                  55                  60

Asp Pro Arg Pro Thr Met Asp Gly Asp Pro Asp Thr Pro Lys Pro Val
65                  70                  75                  80

Ser Phe Thr Val Lys Glu Thr Val Cys Pro Arg Thr Thr Gln Gln Ser
                85                  90                  95

Pro Glu Asp Cys Asp Phe Lys Lys Asp Gly Leu Val Lys Arg Cys Met
            100                 105                 110

Gly Thr Val Thr Leu Asn Gln Ala Arg Gly Ser Phe Asp Ile Ser Lys
        115                 120                 125

Asp Asn Lys Arg Phe Ala Leu Leu Gly Asp Phe Phe Arg Lys Ser Lys
    130                 135                 140

Glu Lys Ile Gly Lys Glu Phe Lys Arg Ile Val Gln Arg Ile Lys Asp
145                 150                 155                 160

Phe Leu Arg Asn Leu Val Pro Arg Thr Glu Ser Asp Tyr Lys Asp Asp
                165                 170                 175

Asp Asp Lys Cys Gln Asp Ser Glu Thr Gly Thr Phe Tyr Gly Ser
            180                 185                 190
```